United States Patent
Stevens et al.

(10) Patent No.: US 9,968,307 B2
(45) Date of Patent: May 15, 2018

(54) SYSTEMS AND METHODS FOR SELECTING PARAMETERS USING CONTRAST AND NOISE

(71) Applicant: General Electric Company, Schenectady, NY (US)

(72) Inventors: Grant Morey Stevens, Cedarburg, WI (US); Roy A. Nilsen, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 453 days.

(21) Appl. No.: 13/726,371

(22) Filed: Dec. 24, 2012

(65) Prior Publication Data

US 2014/0177788 A1   Jun. 26, 2014

(51) Int. Cl.
*A61B 6/00*    (2006.01)
*A61B 6/03*    (2006.01)

(52) U.S. Cl.
CPC ............ *A61B 6/032* (2013.01); *A61B 6/5258* (2013.01); *A61B 6/542* (2013.01); *A61B 6/54* (2013.01)

(58) Field of Classification Search
USPC .................................................. 378/4, 8, 16
See application file for complete search history.

(56) References Cited

U.S. PATENT DOCUMENTS

| | | | |
|---|---|---|---|
| 6,775,352 B2 | 8/2004 | Toth et al. | |
| 7,688,938 B2 | 3/2010 | Paliwal et al. | |
| 7,734,006 B2 | 6/2010 | Miyazaki et al. | |
| 7,813,471 B2 | 10/2010 | Hirokawa et al. | |
| 9,877,696 B2* | 1/2018 | Taki | A61B 6/544 |
| 2005/0031082 A1 | 2/2005 | Haaga et al. | |
| 2007/0116337 A1* | 5/2007 | Toth et al. | 382/128 |
| 2007/0147579 A1 | 6/2007 | DeMan et al. | |
| 2007/0162311 A1* | 7/2007 | Gentles | 705/3 |
| 2011/0317806 A1 | 12/2011 | Eusemann et al. | |
| 2012/0114093 A1* | 5/2012 | Yu et al. | 378/8 |
| 2012/0140893 A1* | 6/2012 | Feuerlein | A61B 6/032 378/108 |

(Continued)

FOREIGN PATENT DOCUMENTS

| | | |
|---|---|---|
| JP | 4954062 B2 | 1/2008 |
| WO | WO 2011008967 A1 | 1/2011 |

*Primary Examiner* — David E Smith
*Assistant Examiner* — James Choi
(74) *Attorney, Agent, or Firm* — Dean D. Small; The Small Patent Law Group, LLC.

(57) ABSTRACT

An imaging system includes an identification module, an analysis module, and a determination module. The identification module is configured to identify a scanning mode of operation. The analysis module is configured to determine an attenuation for an object for a scan to be performed on the object. The determination module is configured to determine an image contrast for each of plural setting combinations, determine a corresponding tolerable noise for the image contrast for each of the setting combinations based on the scanning mode of operation, and determine a corresponding diagnostic dosage for each setting combination, the diagnostic dosages corresponding to the image contrast and tolerable noise for the corresponding setting combination. The determination module is also configured to select an operational setting for the scan to be performed using the dosages determined.

28 Claims, 4 Drawing Sheets

(56) References Cited

U.S. PATENT DOCUMENTS

| | | | |
|---|---|---|---|
| 2012/0201344 A1* | 8/2012 | Feuerlein et al. | 378/4 |
| 2012/0236995 A1* | 9/2012 | Eusemann et al. | 378/108 |
| 2012/0278039 A1* | 11/2012 | Peng | A61B 6/502 |
| | | | 702/181 |
| 2014/0376688 A1* | 12/2014 | Karmazyn | A61B 6/032 |
| | | | 378/8 |
| 2015/0359501 A1* | 12/2015 | Eronen | A61B 6/032 |
| | | | 378/62 |
| 2017/0065244 A1* | 3/2017 | Taki | A61B 6/4291 |

* cited by examiner

SYSTEMS AND METHODS FOR SELECTING PARAMETERS USING CONTRAST AND NOISE

BACKGROUND OF THE INVENTION

The subject matter disclosed herein relates generally to imaging systems and methods, and more particularly, to systems and methods for selecting parameters for imaging.

Computed Tomography (CT) imaging systems typically include an x-ray source and a detector. As the x-rays pass from the source through the object being imaged, the x-rays become attenuated before impinging upon the detector. The intensity of the attenuated beam radiation received at the detector is responsive to the attenuation of the x-rays by the object, with detector elements producing separate electrical signals responsive to the beam attenuation at the detector element location. These electrical signals may be referred to as x-ray attenuation measurements. Further, the x-ray source and the detector array may be rotated around the object to be imaged such that an angle at which an x-ray beam intersects the object changes. A group of x-ray attenuation measurements, or projection data, from a detector at one gantry angle may be referred to as a "view." A set of views made at different gantry angles during one revolution of an x-ray source and detector may be referred to as a "scan." In an axial scan, projection data is processed to construct an image that corresponds to a two-dimensional cross-section or slice of an object being scanned An image may be reconstructed, for example, using a technique referred to as a "filtered back-projection technique." This process converts the attenuation measurements from a scan into discrete integers, ranging from −1024 to +3071, called "CT numbers" or "Hounsfield Units" (HU). These HU's are used to control the brightness of a corresponding pixel on a cathode ray tube or a computer screen display in a manner responsive to the attenuation measurements. This integer conversion, or scoring, allows a physician or a technician to determine the approximate density of matter based on the intensity of the computer display.

Certain scanning parameters, such as x-ray tube, or emitter, current ("mA"), x-ray tube supply voltage ("kV" or "kVp"), slice thickness, scan time, or helical pitch (for helical scans) are known to affect the x-ray beam, which in turn affects image quality. A higher x-ray tube current may, for example, improve image quality (e.g., by reducing image noise), but increase the dosage of radiation received by a patient. Lower x-ray tube current levels may lead to streaking or other artifacts in an image. With regard to x-ray tube voltage, conventional CT scanners may provide for several tube voltage stations (for example, discrete stations ranging between 80 kV to 140 kV) that allow a technician and/or physician to select the x-ray tube voltage. However, conventional voltage selection may be mostly responsive to the preference of the physician, and thus typically may lack sufficient guidance. While on one hand higher tube voltage provides for better geometric dose efficiency for larger patients, lower tube voltage has been shown to provide for better contrasts for different types of materials (e.g., contrast-enhanced lesions). Such tradeoffs may not be well known and, thus, the emitter tube voltage selection is generally fixed for a certain type of scan regardless of the patient size or clinical intent.

In the past, CT scans have been performed, for example, with tube currents adjusted to match a patient size and intended use. In terms of tube voltage, however, little or no adjustment may have been made for patient or usage in certain systems. Because of the interaction of tube voltage and current, image quality may suffer and/or unacceptable levels of noise may be present in scans for which tube voltage has been adjusted. Further, selection of tube voltage may be difficult, complicated, or poorly explained, so that the lack of ease of use has resulted in practitioner's often failing to adjust a tube voltage for a particular patient or procedure. Because of the complexity, for example, of interactions between aspects of systems and/or between parameters defining the operation of scanning systems, it is difficult to adjust tube voltage, for example to optimize radiation dose while maintaining tolerable image quality. Therefore, non-optimal usage of a scanning system may result.

BRIEF DESCRIPTION OF THE INVENTION

In one embodiment, an imaging system is provided. The imaging system includes an identification module, an analysis module, and a determination module. The identification module is configured to identify a scanning mode of operation. The analysis module is configured to determine an attenuation for an object for a scan to be performed on the object. The determination module is configured to determine an image contrast for each of plural setting combinations, determine a corresponding tolerable noise for the image contrast for each of the setting combinations based on the scanning mode of operation, and determine a corresponding diagnostic dosage for each setting combination, the diagnostic dosages corresponding to the image contrast and tolerable noise for the corresponding setting combination. The determination module is also configured to select an operational setting for the scan to be performed using the dosages determined.

In another embodiment, a method (e.g., a method for selecting settings for a scan to be performed on an object) is provided. The method includes identifying a scanning mode of operation. The method also includes determining an attenuation for the object for the scan to be performed, determining an image contrast for each of plural setting combinations, and determining a corresponding tolerable noise for the image contrast for each of the setting combinations. Further, the method includes determining a corresponding diagnostic dosage for each setting combination, the diagnostic dosages corresponding to the image contrast and tolerable noise for the corresponding setting combination. Also, the method includes selecting an operational setting for the scan to be performed using the dosages determined.

In a further embodiment, a tangible and non-transitory computer readable medium is provided. The tangible and non-transitory computer readable medium includes one or more computer software modules configured to direct a processor to identify a scanning mode of operation, determine an attenuation for an object for a scan to be performed, determine an image contrast for each of plural setting combinations, and determine a corresponding tolerable noise for the image contrast for each of the setting combinations. The one or more computer software modules are also configured to direct a processor to determine a corresponding diagnostic dosage for each setting combination, the diagnostic dosages corresponding to the image contrast and tolerable noise for the corresponding setting combination. Further, the one or more computer software modules

DETAILED DESCRIPTION OF THE INVENTION

The foregoing summary, as well as the following detailed description of various embodiments, will be better understood when read in conjunction with the appended drawings. To the extent that the figures illustrate diagrams of the functional blocks of the various embodiments, the functional blocks are not necessarily indicative of the division between hardware and/or circuitry. Thus, for example, one or more of the functional blocks (e.g., processors or memories) may be implemented in a single piece of hardware (e.g., a general purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings.

Described herein are various embodiments, for example, for selecting operational parameters to be used to perform a scan (e.g., a CT scan). A predetermined relationship or balance between a first image quality metric and a second image quality metric may be used to determine an allowable adjustment of one or more operational parameters of a scan. Various embodiments use a predetermined or otherwise defined relationship and/or predetermined balancing criteria corresponding to a balance between image contrast (and/or change thereof) and tolerable image noise (and/or change thereof) to determine and/or adjust one or more operational parameters, such as tube current (mA), tube voltage (kV or kVp), amount(s) and/or type(s) of contrast agent(s), or the like. The operational parameters may be selected based on a relationship between contrast and noise. Further, the settings for a scan may be selected to reduce or minimize a diagnostic dosage. The diagnostic dosage may include one or more of radiation resulting from a scan or a dosage of contrast agent administered to a patient (or a weighted combination of both).

The imaging parameters may be selected to allow a degradation of one type of image quality metric resulting from a change in one parameter (e.g., a noise level corresponding to a tube current or mA) as a trade-off for an improvement of a different type of image quality metric due to a corresponding change in a second parameter (e.g., an image contrast corresponding to a tube voltage or kV). In some embodiments, the amount of increase in noise permitted based on an increase in image contrast may be based on a scaling relationship between an increase in contrast and a permitted increase in noise. Additionally or alternatively, the relationship between contrast and permitted or tolerable noise may be determined using one or more coefficients or factors corresponding to a weighted combination of a plurality of materials expected to be encountered during the scan to be performed. The particular form of the relationship may be determined based on an identified mode of operation (e.g., clinical task or application corresponding to a scan) that corresponds to one or more of a type of equipment used to acquire imaging data, a type of software used to reconstruct an image, a type of tissue or tissues encountered by a scan, the presence of contrast agent, the type and/or amount of contrast agent if present (or types and/or amounts of multiple contrast agents if multiple contrast agents present), user preferences (e.g., certain users may place a higher priority on improved contrast while others may place a higher priority on reduced noise), or the like. In some embodiments, materials not present during a scan or not physically achievable may be utilized to determine an appropriate relationship to yield the desired dosage and image quality performance.

A technical effect of at least one embodiment includes the reduction or minimization of a potentially harmful, inconvenient, expensive, or otherwise undesirable diagnostic dosage. Also, a technical effect of at least one embodiment includes improvement in the balance of or tradeoff between image noise and contrast for a reduced dosage of radiation and/or contrast agent. Further, a technical effect of at least one embodiment includes improvement of ease of use of tube voltage selection. For example, embodiments provide for the automatic selection or adjustment of at least one of tube voltage, tube current, noise index, bowtie filter, field of view, or image reconstruction approach to reduce or minimize diagnostic dosage. A technical effect of at least one embodiment includes improvement in selection of tube voltage and/or current settings based on one or more of a patient size or other characteristic, a mode or clinical task associated with a scan, a type of tissue or tissues, practitioner characteristics or preferences, or the like. A technical effect of at least one embodiment includes the selection of imaging parameters to produce a reconstructed image having one or more image quality characteristics (e.g., contrast, noise, or the like) tailored for particular practitioners (e.g., based on equipment used by the practitioners, individual preferences of practitioners or groups of practitioners, or the like).

Figure 1:
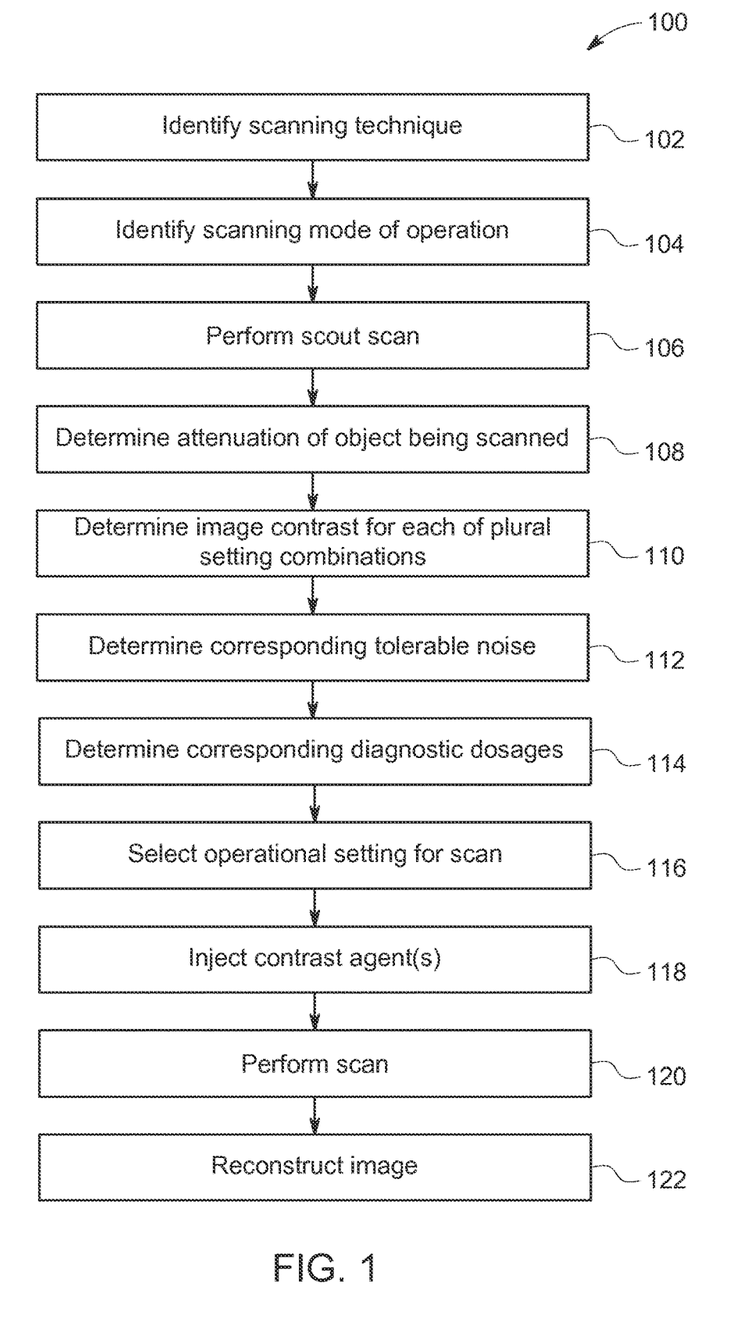
FIG. 1 is a flowchart of an exemplary method for reconstructing an image of an object in accordance with various embodiments.

FIG. 1 is a flowchart of a method 100 for reconstructing an image of an object in accordance with various embodiments. Although the method 100 is described in a medical setting using a Computed Tomography (CT) imaging system, it is contemplated that the benefits of the various embodiments described herein may accrue to all x-ray based systems, such as x-ray systems, dual energy x-ray absorptiometry (DEXA) systems, vascular systems, interventional systems, fluoroscopy systems, or the like. The method 100, for example, may also be employed in the context of industrial CT imaging systems such as a baggage scanning CT system typically used in a transportation center such as, for example, but not limited to, an airport or a rail station. The method 100, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 102, a scanning technique is identified. For example, the scanning technique may be a reference scanning technique corresponding to reference scanning settings such as tube voltage or tube current. In various embodiments, the reference scanning technique identifies one or more settings of a scanning device, such as a tube voltage, a tube current, or the like. Such a reference scanning technique may be used to help define or describe an image quality that is expected, required, preferred, desired, or the like by a practitioner. Identification of a scanning technique using or corresponding to a user input may help identify an image quality expected or preferred by user, and can be used so that any adjustments to operational scanning parameters such as tube current or voltage may be made so that a desired or expected image quality is maintained or an equivalent image quality is provided. One or more image qualities or characteristics corresponding to the reference scanning technique may be employed as a baseline from which adjustments may be made. For example, a baseline contrast and baseline noise index may be determined for a reference scanning technique. Adjustments to tube voltage and/or current may then be evaluated by determining an amount of change in the contrast and noise resulting from such adjustments from the baseline. Further, in various embodiments, only adjustments to the tube voltage and tube current that satisfy one or more thresholds of change may be evaluated as a potential setting for an actual scan to be performed. For example, an improvement in contrast may have to satisfy a first threshold while a degradation in noise may have to satisfy a second threshold. The first and second thresholds may be described in terms of a percentage change from a baseline corresponding to a reference scanning technique. The first and second thresholds may be different from each other.

The scanning technique may be identified based, for example, on a user input, a determination made autonomously in response to a user input, or a combination thereof. Consider various embodiments in which the identified scanning technique includes a tube voltage and a tube current. In one example scenario, a user may input both a tube voltage and a tube current. In this first example scenario, the scanning technique includes manually entered information. In a second example scenario, a user may input a tube voltage and a noise index. Generally, tube current relates to noise index, with higher tube currents corresponding to less noise in a resulting image. In this second example scenario, a tube current may be autonomously selected using the manually entered noise index, so that the second example scenario uses an identified scanning technique including a value manually entered (e.g., tube voltage) as well as a value autonomously determined (e.g., tube current). In a third example scenario, a user may input a task to be performed and/or a protocol corresponding to a task to be performed. For example, a user may input information corresponding to a scan to be performed of a patient's head. In some embodiments, more specific information regarding a patient or procedure may also be entered. A standard protocol for that particular user may specify that head scans are to be performed at 120 kV and 200 mA. Thus, a scanning system may autonomously identify the scanning technique as including a 120 kV tube voltage and a 200 mA tube current. In the third example scenario, the scanning technique thus includes autonomously determined information.

In various embodiments, the user input may be input via use of a keypad, dial, touchscreen, or the like that allows a user to specify a particular value of a given parameter, such as voltage, current, noise index, or the like. Alternatively or additionally, a user may be presented with a series of values for a particular parameter from which a selected value may be chosen. For example, a user may be presented with a choice between various tube voltage settings or stations (e.g., a user may select one of a 80 kV setting, a 100 kV setting, a 120 kV setting, or a 140 kV setting). In other embodiments, other values of voltage may be selectable additionally or alternatively, or voltage may be varied substantially continuously.

By way of example, tube voltages in some embodiments may range between about 80 kV to about 140 kV. Tube current may vary from about 10 mA to about 800 mA. A noise index may range from about 5 to about 100. For example, a reference setting including a tube voltage of about 120 kV and a noise index of about 13 may be input by a user. (A tube current may be determined based on the noise index.) The ranges discussed herein are intended by way of example, and are not intended to limit or exclude the use of different parameters or ranges in other embodiments.

At 104, a scanning mode of operation is identified. Generally, the mode of operation may include or specify one or more factors or parameters that may influence the relationship between a change in contrast and change in tolerable noise. The scanning mode of operation may correspond to, for example a clinical task, clinical application, or the like, to be performed and/or particular aspects of or associated with the clinical task to be performed. The mode of operation may include, specify, or otherwise correspond to one or more of a type of tissue to be scanned, a type of tissue within a scanned region to be analyzed, a portion of the body to be scanned, a type of information to be acquired via the scan and/or the purpose of a scan (such as an angiogram, or, as another example, the identification or analysis of a lesion), an indication of whether or not contrast agent is used, a type of contrast agent used, an amount of contrast agent used, age of patient (e.g., adult, pediatric, newborn, child, young adult), or the like. The scanning mode of operation and/or scanning reference technique may be identified directly or directly using information input by a practitioner. For example, a practitioner may input one or more of a tube voltage, tube current, noise index, portion of body to be scanned, purpose of scan, or the like.

As another example, the scanning mode of operation may be identified, for example, at the same time that the reference scanning technique is identified via the entry or identification of a protocol. A practitioner may specify (e.g., select from a list) a particular protocol (e.g., angiogram, liver scan, head injury, lesion analysis, sinus study, brain scan, chest scan, chest scan for identification of potential tumors, chest scan for identification of fluid accumulation, or the like), and the scanning mode of operation may be determined based on the specified protocol. In various embodiments, protocols may be specified at varying levels of specificity. For example, a protocol may indicate a portion of the body to be scanned, or may indicate a portion of the body to be scanned as well as the purpose of the scan.

At 106, a scout scan is performed. A scout scan may be understood as a preliminary scan of an object performed at a lower tube voltage and/or lower tube current setting and having a reduced radiation dosage compared to a scan to be performed for diagnostic purposes (e.g., a diagnostic scan). A scout scan may be used, for example, to determine an attenuation for the object (e.g., region of interest of a patient) being scanned. In some embodiments, the results of a scout scan may be used along with a diagnostic scan for analysis and diagnosis, while in other embodiments the results of a scout scan may not be so used.

At 108, an attenuation (e.g., attenuation associated with a region of interest being scanned) is determined. For example, a patient attenuation corresponding to or characterizing the ability or tendency of a patient (or a region of interest of a patient) to attenuate an x-ray beam directed through the patient (or region of interest) may be determined. In the embodiment depicted in FIG. 1, the attenuation is determined using information acquired during the scout scan at 106. In other embodiments, additionally or alternatively, the attenuation may be determined using alternate techniques. For example, the attenuation may be calculated, estimated, or otherwise determined using one or more of a patient height, patient weight, patient body mass index (BMI), patient diameter, or the like.

At 110, an image contrast (e.g., expected level of contrast in an image acquired from a scan) is determined for each of plural setting combinations. One or more parameters may be varied across the plural setting combinations. For example, a different tube voltage may be used to define each setting combination. As another example, the use of contrast agent (including amount and/or type) may be varied across setting combinations for which image contrast is determined. As another example, both tube voltage and contrast agent may be varied across a group of plural setting combinations, with image contrast determined for each of the setting combinations.

The image contrast (or other image quality metric) may be expressed or specified as an absolute value and/or as a percentage change from a baseline, such as an image contrast resulting from a setting combination corresponding to a reference scanning technique (e.g., an image contrast for a reference scanning technique identified at 102).

In some embodiments, the image contrast (or other image quality metric) may be determined from a specified operational parameter of a scanning procedure. The image contrast may be determined using, for example, the tube voltage in conjunction with the attenuation determined at 108. The image contrast may be determined, for example, using a lookup table calibrated using standardized values or using values determined from clinical studies. In other embodiments, the image contrast may be determined using a mathematical relationship, for example, an equation or algorithm using tube voltage and attenuation as inputs and providing an image contrast as a result.

In one example scenario, image contrast for four different setting combinations (e.g., four different voltage levels) is provided in the table below. For the purposes of developing the table, the object to be scanned is an acrylic cylinder having a diameter of about 32 centimeters. Such an object used to characterize the radiation dose performance of a scanner may be referred to as a phantom. The phantom was evaluated using a General Electric Discovery CT750 HD scanner. For the table, iodine contrast as a function of tube voltage was determined. It should be noted that, while iodine is used in the presently discussed example scenario, other materials may be used alternatively or additionally. For the example scenario, one bowtie filter was used during scanning, and the 120 kV setting was considered as the baseline or reference scanning technique, with contrast for a given setting expressed as a percentage change from the baseline.

| Tube Voltage (kVp) | Relative Image Contrast (%) |
|---|---|
| 80 | 164% |
| 100 | 124% |
| 120 | 100% |
| 140 | 86% |

In the example scenario, the highest contrast (164% of the baseline) is observed for a setting combination including a tube voltage of 80 kVp, while the lowest contrast (86%) is observed for a setting combination including a tube voltage of about 140 kVp. Thus, for the scanning of the phantom in the example scenario, some amount of increased noise level relative to the baseline or reference scanning technique may be tolerable for a scan performed at the 80 kVp setting due to the increased image contrast, while a reduced amount of noise relative to the baseline or reference scanning technique may be tolerable at the 140 kVp level.

At 112, a corresponding tolerable noise is determined. The corresponding tolerable noise in the illustrated embodiment is the amount of noise (or increase in noise) that may be permitted, tolerated, or accepted for a given amount of image contrast (or increase in image contrast). A separate corresponding tolerable noise is determined for each of the setting combinations. Thus, in the illustrated embodiment, for each setting combination, there will be determined a corresponding image contrast and corresponding noise level. The image contrast/noise level pairing for each setting combination may be thought of as an image contrast/noise combination that provides an image quality for the particular setting combination that is equivalent to the image quality obtained using a baseline or reference scanning technique for a given mode of operation. The corresponding tolerable noise may be determined using a relationship that describes the amount of noise increase that may be tolerated in exchange for an amount of contrast improvement over a range of voltages for a given mode of operation. The particular relationship may depend on one or more of the equipment used to perform a scan and/or reconstruct an image (e.g., the ability of software used to reconstruct an acquired image to counter noise or remove artifacts), the particular user (e.g., different users may have different tolerances for noise), the object being scanned (e.g., different materials may have attenuations that vary more or less across voltages), contrast agent (e.g., whether or not one or more contrast agents are present, amount of each contrast agent, type of each contrast agent), patient size, or the like Thus each mode of operation may include one or more aspects of such information, and a separate relationship (e.g., format of mathematical relationship, factors or coefficients employed, or the like) for each mode (or group of modes) may be determined or defined, so that identification of a mode of operation allows identification and use of an appropriate corresponding relationship between contrast and noise to determine an adjustment in operational parameters of a scan (e.g., tube voltage, tube current, amount of contrast agent(s) present, image reconstruction approach) that will provide an acceptable image quality while reducing a diagnostic dosage (e.g., radiation).

A given relationship may be tailored or customized for a particular procedure and/or practitioner, allowing an adjustment (e.g., change in tube voltage or tube current) to lower a diagnostic dosage, while still providing an image conforming to a particular practitioner's expectations, preferences, or demands for image quality based on an identified reference technique. A particular relationship between contrast and noise may correspond to a single material, or may correspond to a combination of materials (e.g., a relationship based on a weighted combination of materials, such as 80% soft tissue and 20% iodine). A weighted relationship may be determined from a clinical study corresponding to the weighted combination, or may be extrapolated or otherwise determined from relationships defined for the individual materials. Because the relationship between image contrast and tolerable noise may vary by material, accounting for the presence of multiple materials by such a weighting may provide a more useful relationship for a given scanning mode of operation. Additionally or alternatively, use of a scaling relationship between tolerable noise and image contrast may be employed in various embodiments.

Consider two different scans of a patient that may be performed using different operational parameters. For the purposes of the present discussion, two scans performed using different tube voltages will be discussed, although the general principles discussed herein may also apply to different parameters or combinations of parameters. Aspects of image quality that can vary between the scans taken at different voltages may include, for example, image contrast and noise. For the present discussion, it may be assumed that other factors, such as spatial resolution, temporal resolution, or the like, are not significantly or substantially changed. Thus, it may possible to use a contrast to noise ratio (CNR) as a metric to evaluate the image quality for the images.

The CNR of a region of interest may be defined as the ratio of the relative signal to the background noise. In order to maintain the image quality of an image when the tube voltage is changed, in one approach, one could theoretically require that the CNR remain the same. If the change in contrast due to the voltage change can be determined or otherwise characterized, then a change in noise to maintain CNR may be easily determined, as the noise may be allowed to increase at the same percentage or amount of change as the change in contrast. It may be noted at this time that the particular contrast resulting from a given tube voltage may be dependent on a variety of factors, including patient size, equipment being used (e.g., number and/or type of bowtie filter employed), or other factors that may impact the x-ray spectrum being transmitted through a patient.

Maintaining the CNR at a constant level, however, may have drawbacks that result in lower image quality and/or unnecessarily high radiation dosages, for example. With reference to the table above, in the above discussed example scenario, a change from 120 kV to 80 kV may result in an increase in contrast of 64%. Thus, to maintain a constant CNR, a noise index may be allowed to increase 64% as well. For certain clinical tasks or scanning modes, this may provide an acceptable image quality. For example, in a situation where a practitioner is only interested in looking at iodine images in the region (the values in the table were developed for iodine contrast), such an increase may result in a usable or otherwise acceptable image. However, for other modes or clinical applications, a practitioner may have interest in soft tissue regions of the image. For such regions, image contrast may not change to the same degree for a change in tube voltage as was observed for iodine (e.g., due to the relative insensitivity of soft tissue x-ray attenuation to variations in x-ray energy). The soft tissue regions, however, will still be degraded by increased image noise resulting from the above indicated 64% increase in noise index compared to the baseline 120 kV scan of the example. Such an increase in noise may result in an unacceptable image.

As a result, maintenance of a constant CNR may not be as effective as desired in providing image quality and/or reducing a diagnostic dosage. Thus, embodiments may utilize different methods for determining or using a relationship correlating a change in contrast and an acceptable change in noise. For example, embodiments may describe relationships between contrast and acceptable noise levels (or between changes in contrast and changes in acceptable noise from a baseline reference) that take into account factors such as a particular mode of scanning operation or clinical task being performed. Furthermore, some embodiments may describe relationships to vary contrast and/or noise levels in a defined mathematical fashion (e.g., continuously) between tube voltage settings or stations in order to produce acceptable transitions between acquisition set points.

If some information is known regarding what particular structures a practitioner is trying to see, what aspects of an image are of particular interest to a practitioner, what purpose the scan is being used for, or the like, settings may be appropriately selected to provide an acceptable image quality while adjusting tube voltage. For example, allowing a relatively larger increase in noise may be permissible to match an increase in iodine contrast may be acceptable for modes where the region of interest is generally limited to iodine, such as angiograms. Such a relatively large increase in noise may not be permissible in other modes or tasks, such as liver scans. Embodiments take into account the mode (e.g., clinical task) when determining a permissible amount of change in noise relative to a change in image contrast (e.g., an image contrast level for iodine) due to a change in tube voltage.

For example, one or more techniques may be employed to determine or define a relationship between a change in contrast and a change in acceptable noise level. For example, a constraint to one or more of the changes may be employed, such as an upper limit on a permissible amount of noise increase. As another example, noise may be allowed to increase as a percentage of contrast increase. The particular percentage relationship may vary by mode or task (e.g., including one or more of tissue being scanned and/or analyzed, purpose of scan, presence of contrast agent, or the like). As one more example, a weighting of multiple materials that may be encountered during a scan may be considered. As yet another example, the relationship between change in contrast and noise level may be described by a mathematical relationship that raises one or more of contrast or noise to an exponential power. It should be noted that the above approaches are not intended as exclusive of each other, and one or more may be used in conjunction with each other.

To determine any particular specific contrast/noise relationship (e.g., the format of the relationship, particular values of coefficients or parameters, or the like), a variety of factors may be considered. For example, a noise tolerance for each mode may be assessed. In some embodiments, some modes may be grouped together. For example, modes or tasks that have relatively higher noise tolerance may allow relatively higher changes in acceptable noise level relative to contrast changes. As another example, factors regarding a particular practitioner (or group of practitioners) may be used. Such factors may include personal preferences, as one practitioner may have a preference or tolerance for image noise that differs from other practitioners. As another example, a practitioner may use a particular type of software that is relatively good (or relatively poor) at addressing and removing noise or other artifacts. For practitioners using equipment and/or software that is relatively good at addressing noise when reconstructing an image, a relatively higher increase in noise corresponding to improvements in image contrast may be allowed. One or more of these factors may be included or otherwise accounted for when specifying or identifying the scanning mode of operation at 104.

Information used to determine a particular contrast/noise relationship may be gathered, for example, at protocol definition, during a clinical trial or other study, or the like. For example, image contrast and acceptable noise levels for a variety of acceptable images may be tabulated against factors such as scanning mode (and/or one or more aspects of scanning mode such as tissue type, presence of contrast agent, or the like), tube voltage, attenuation, or the like. Particular relationships to be used for a given mode may then be extrapolated, estimated, or otherwise determined using the data points obtained in a clinical study. The clinical study may, in some embodiments, be performed using preferences of a particular group of practitioners. In other embodiments, any particular coefficient or parameter determined in the study may be determined as a range instead of a particular value, with selection of a value from a particular portion of the range used to customize or tailor the relationship for a given practitioner or group of practitioners.

The image contrast/tolerable noise relationship for a given mode may be expressed as a mathematical expression correlating a change in contrast to a change in acceptable or tolerable noise in some embodiments, while values may be tabulated in a look-up table in other embodiments. The particular relationship or tabulated values may be based, for example, on a calibrated clinical study correlating variations in image contrast and noise across ranges of settings for one or more scanning modes of operation. In some embodiments, the image contrast/tolerable noise relationship may be expressed in terms of percentage changes of image contrast and tolerable noise from a baseline (e.g., corresponding to a reference setting), while in other embodiments the relationship may be expressed in terms of absolute values of noise and image contrast. Generally, with a scanning mode of operation and corresponding image contrast/tolerable noise relationship identified, and contrast values at each voltage level determined, the acceptable noise (from which tube current may be determined) for each voltage level may be determined using the particular relationship between contrast and noise specified for the identified mode.

As one example of a particular relationship, a scaling relationship will now be discussed. Such a scaling approach may be based on a trade-off of a first percentage variation of a first image quality parameter (e.g., image contrast) for a second percentage variation of a second image quality parameter (e.g., noise level), with one or more scaling factors specifying a rate at which the image quality parameters vary relatively to each other. In one example scenario, the scaling relationship corresponds to a scaling factor described by $sf=\Delta NI/\Delta IC$, where sf is the scaling factor, $\Delta IC$ corresponds to a change in image contrast, and $\Delta NI$ corresponds to an acceptable increase in noise corresponding to an increase in image contrast. Rearranging the terms, the acceptable increase in noise may be expressed as $\Delta NI=sf*\Delta IC$. Different scaling factors may be used for different modes of operation. For example, for a mode of operation corresponding to a soft tissue, contrast-enhanced scan, the scaling factor sf may be about 0.33. Thus, for the soft tissue, contrast-enhanced scan, the tolerable noise is allowed to increase at about one-third the rate of increase in image contrast. Thus, if a given tube voltage adjustment provides an improvement in image contrast of 90%, the tolerable noise level for the soft tissue, contrast-enhanced scan may be allowed to increase 30% (e.g., 0.33*90%=30%). For a different mode of operation, such as a mode corresponding to a different material and/or lack of contrast agent, a different scaling factor may be used. The table below provides an example using the voltage and image contrast values from the previously discussed table, and allowing tolerable noise to vary about ⅓ as much as image contrast. In the below table, tolerable noise is expressed as a percentage level of a baseline tolerable noise corresponding to a 120 kVp tube voltage setting.

| Tube Voltage (kVp) | Image Contrast (%) | Tolerable Noise (%) |
|---|---|---|
| 80 | 164% | 121% |
| 100 | 124% | 108% |
| 120 | 100% | 100% |
| 140 | 86% | 95% |

In various embodiments, a scaling factor may be presented as a range or family of scaling factors. For example, instead of a scaling factor of 0.33 for the above example, the scaling factor for a given mode may be presented as a range or family of values varying from 0.25 to 0.40. Users that have higher tolerance for noise and/or lower tolerance for diagnostic dosages such as radiation may use a scaling factor value from the upper end of the range (e.g., at or about 0.40) when determining tolerable noise, users with lower tolerance for noise and/or higher tolerance for diagnostic dosages such as radiation may use a scaling factor value from the lower end of the range (e.g., about 0.25), while still other users may employ intermediate values (e.g., 0.30, 0.33, 0.35, or the like). Alternatively or additionally, the scaling factor may be derived using a weighted approach. For example, for a scanning mode of operation using a combination of iodine and soft tissue, a combined scaling factor may be determined using weighted contributions of a first scaling factor corresponding to soft tissue and a second factor corresponding to iodine, with the particular weightings of the first and second scaling factors depending on the relative proportions of iodine and soft tissue in a region of interest.

Thus, an equivalent or acceptable image quality may be determined and achieved across a range of operational parameter (e.g., tube voltage) values while not necessarily maintaining a constant CNR (or, put another way, allowing the CNR to vary).

At 114, corresponding diagnostic dosages are determined for each setting combination. For example, each setting combination may specify a tube voltage. Further, a corresponding tolerable noise level for each setting combination may be known (e.g., determined at 112). A tube current corresponding to each tolerable noise level may then be determined, for example using conventional techniques correlating tube current to noise level or index. Thus, for each setting combination, a tube voltage and a tube current may be known. A radiation dosage resulting for the tube voltage and tube current combination may then be determined using conventional techniques. Thus, a radiation dosage for each setting combination may be determined in the illustrated embodiment. In other embodiments, other diagnostic dosages (e.g., amount of contrast agent either alone or in combination with a radiation dosage) may be determined. The table below provides an example using the voltage, image contrast, and tolerable noise values from the previously discussed tables. In the below table, corresponding first dosage levels (e.g., radiation) are represented as A, B, C, D and second dosage levels (e.g., contrast agent) are represented as P, Q, R, S for the various tube voltage settings.

| Tube Voltage (kVp) | Image Contrast | Tolerable Noise | Dosage 1 | Dosage 2 |
|---|---|---|---|---|
| 80 | 164% | 121% | A | P |
| 100 | 124% | 108% | B | Q |
| 120 | 100% | 100% | C | R |
| 140 | 86% | 95% | D | S |

At 116, an operational setting for a scan to be performed is selected using the dosages determined at 114. In some embodiments, an operational setting may correspond to a setting combination used to determine image contrast that corresponds to a preferred dosage as discussed herein, along with one or more parameters such as tube current that provides acceptable noise for the particular tube voltage. For example, an operational setting (e.g., a combination of tube voltage and tube current) providing the lowest diagnostic dosage (e.g., lowest radiation exposure) may be selected. As another example, the operational setting providing the lowest dosage while satisfying a constraint may be selected. In some embodiments, the operational setting may not be varied from the reference setting unless a threshold reduction in dosage is achieved. For example, while an adjustment resulting in a relatively small reduction in dosage may meet the overall needs of a user, the inconvenience of different image appearance and/or need for additional post-scanning processing of an image may not be justified by a small improvement in dosage. In some embodiments, for example, an operational setting may not be varied from a reference setting (e.g., a reference setting provided or identified at 102) unless a reduction of about 10% in radiation exposure may be achieved. In different embodiments, different thresholds may be employed. As another example, system capabilities may provide a constraint on operational setting selection.

Implementation of an automatically selected operational setting (e.g., tube current, tube voltage, type of contrast agent, amount of contrast agent, or the like) may be fully autonomous (e.g., performed without operator intervention) in some embodiments, and not fully autonomous in other. For example, an operational setting selected or specified by a control module or the like may be presented to a practitioner via a prompt on a display or touch screen or the like. The practitioner may then have the option of choosing the automatically selected operational setting or a different operational setting. In some embodiments, the automatically selected operational setting may act as a default setting that may be overridden by intervention by a practitioner.

At 118, a contrast agent (if desired or called for) is introduced to the patient being scanned. The contrast agent may be injected into the patient. In some embodiments, an automated injector may operate in conjunction with a scanning system to autonomously control administration of a contrast agent or agents. In some embodiments, instructions may be provided to a user manually changing or controlling an amount of contrast agent or agents administered to a patient.

At 120, a scan is performed on the object. The scan may be performed using the operational setting selected at 116. The operational setting may include one or more of a tube voltage, tube current, contrast agent (presence, type, and/or amount), or the like. Scanning information or data may be acquired during the scan from a detector upon which x-rays impinge after passing through the object.

At 122, an image is reconstructed. The image corresponds to the object (e.g., patient) being scanned, and may be reconstructed using scanning information or data obtained during performance of the scan at 120. Once reconstructed, the image may be analyzed by a practitioner to diagnose a condition of a patient that has been scanned.

Figure 2:
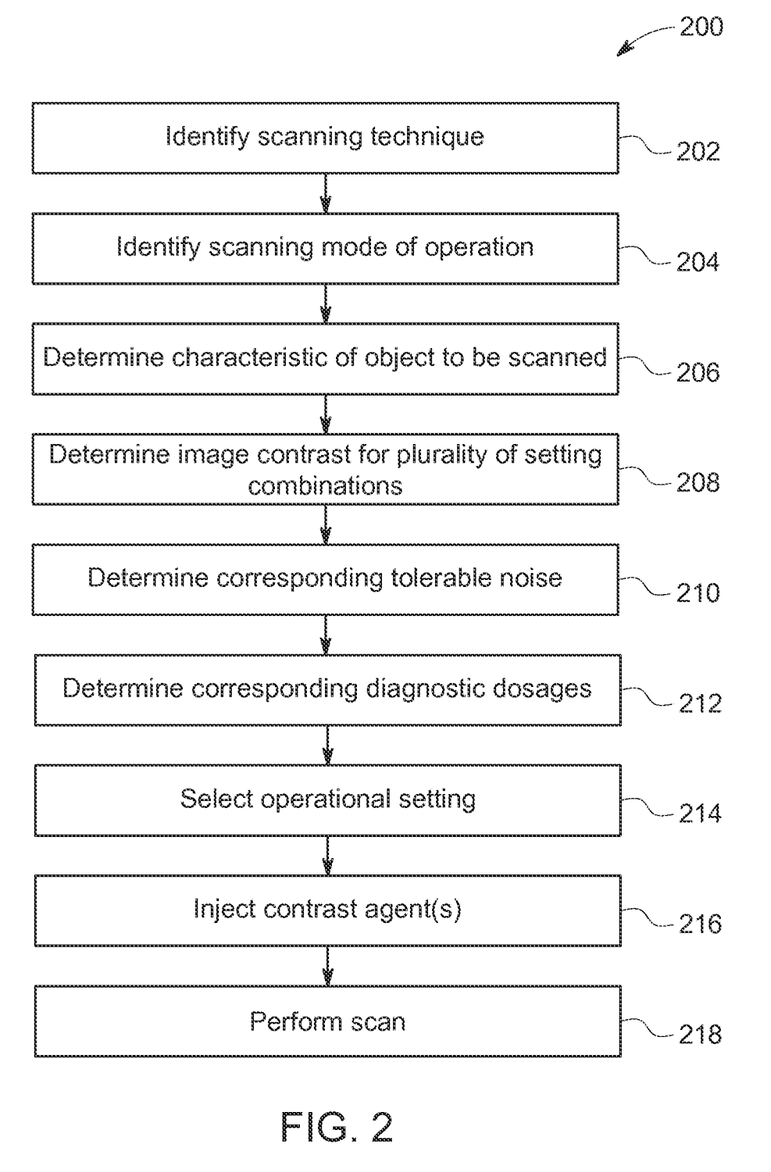
FIG. 2 is a flowchart of an exemplary method for reconstructing an image of an object in accordance with various embodiments.

FIG. 2 is a flowchart of a method 200 for reconstructing an image of an object in accordance with various embodiments. Although the method 200 is described in a medical setting using a Computed Tomography (CT) imaging system, it is contemplated that the benefits of the various embodiments described herein may accrue to all CT imaging systems. The method 200, for example, may employ structures or aspects of various embodiments (e.g., systems and/or methods) discussed herein. In various embodiments, certain steps may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion.

At 202, a scanning technique is identified. The scanning technique may be identified similarly in respects to the identification discussed above in connection with step 102 of the method 100. The scanning technique may be a reference scanning technique. In various embodiments, the reference scanning technique identifies one or more settings of a scanning device, such as a tube voltage, a tube current, or the like, and/or one or more additional settings corresponding to a scan, such as the use of contrast agent, a type of contrast agent, an amount of contrast agent, or the like. The reference scanning technique may be used to help define or describe an image quality that is expected, required, preferred, desired, or the like by a practitioner. Adjustments to tube voltage and/or current may then be evaluated by determining an amount of change in the image contrast and noise resulting from adjustments from the baseline reference scanning technique. The scanning technique may be identified based, for example, on a user input, a determination made autonomously in response to a user input, or a combination thereof.

At 204, a scanning mode of operation is identified. The identification at 204 may be similar in respects to the identification at 104 of the method 100. Generally, the scanning mode of operation may include or specify one or more factors or parameters than can influence the relationship between a change in contrast and change in tolerable noise. For example, the scanning mode of operation may include, for example a clinical task, clinical application, or the like, to be performed and/or particular aspects of or associated with the clinical task to be performed. The mode of operation may include or correspond to one or more of a type of tissue to be scanned, a type of tissue within a scanned region to be analyzed, a portion of the body to be scanned, a type of information to be acquired via the scan and/or the purpose of a scan (such as an angiogram, or, as another example, the identification or analysis of a lesion), an indication of whether or not contrast agent is used, a type of contrast agent used, an amount of contrast agent used, or the like. The scanning mode of operation and/or scanning reference technique may be identified directly or directly using information input by a practitioner. For example, a practitioner may input one or more of a tube voltage, tube current, noise index, portion of body to be scanned, purpose of scan, or the like.

At 206, a characteristic of the object to be scanned is determined. For example, the characteristic may correspond to an attenuation for a region of interest of a patient to be scanned and analyzed or diagnosed, a size of the patient, or the like. A plurality of characteristics may be determined in some embodiments. Alternatively or additionally, a determined characteristic may be a composite characteristic corresponding to a combination of two or more of an attenuation, a patient diameter, a patient BMI, a patient weight, or the like. The attenuation may describe the behavior of the region of interest with respect to the passage of x-rays therethrough. Alternatively or additionally, the characteristic may also include one or more parameters relating to the tolerance of a patient for one or more contrast agents.

At 208, an image contrast (e.g., expected level of contrast in an image acquired from a scan) is determined for each of plural setting combinations. One or more parameters such as tube voltage, presence of image contrast, type of image contrast, amount of image contrast, or the like may be varied across the plural setting combinations. For example, a different amount of a particular contrast agent may be used to define each setting combination. As another example, a tube voltage may be varied across setting combinations for which image contrast is determined. As another example, both tube voltage and amount of contrast agent may be varied across a group of plural setting combinations, with image contrast determined for each of the setting combinations.

At 210, a corresponding tolerable noise is determined. The corresponding tolerable noise in the illustrated embodiment is the amount of noise (or increase in noise) for a given amount of image contrast (or increase in image contrast). A separate corresponding tolerable noise is determined for each of the setting combinations. Thus, in the illustrated embodiment, for each setting combination, there will be determined a corresponding image contrast and corresponding noise level. The various image contrast/noise level pairs for each setting combination may be thought of as an image contrast/noise combination that provides an image quality that is equivalent to the image quality obtained using a baseline or reference scanning technique for a given mode of operation. For example, in one example scenario, the amount of contrast agent is varied across a number of setting combinations while the tube voltage is held constant for a given mode. Generally, higher image contrast will be provided for setting combinations using greater amounts of contrast agent. The corresponding tolerable noise may be determined using a relationship that describes the amount of noise that may be tolerated in exchange for an amount of image contrast improvement over a range of amounts of contrast agent for a given mode of operation. In another example scenario, both amount of contrast agent and tube voltage may be varied. The particular relationship between image contrast and noise may depend on one or more of equipment used to perform the scan and/or reconstruct an image using data collected during the scan, particular user tolerances and/or preferences, object being scanned, contrast agent, patient size, or the like.

At 212, corresponding diagnostic dosages are determined for each setting combination. The determination at 212 may be performed similarly in respects to the determination at 114 discussed above. In some embodiments, each setting combination may specify an amount of a particular contrast agent. Additionally or alternatively, each setting combination may specify a tube voltage. With a corresponding tolerable noise level for each setting combination already determined at 210, a diagnostic dosage (e.g., amount of contrast agent and/or radiation resulting from specified tube current and voltage for a particular setting) may be determined for each setting combination. The diagnostic dosage may include, for example, an amount of contrast agent used, an amount of radiation exposure corresponding to the scan, or a combination (weighted or otherwise) thereof. In alternate embodiments, other parameters and/or dosages may be considered additionally or alternatively.

At 214, an operational setting for a scan to be performed is selected using the dosages determined at 212. In some embodiments, an operational setting may correspond to a setting combination used to determine image contrast that corresponds to a preferred dosage as discussed herein, along with one or more parameters that provides acceptable noise for the particular setting combination. In some embodiments, an operational setting (e.g., a combination of tube voltage, tube current, and amount of contrast agent) providing the lowest diagnostic dosage (e.g., lowest amount of contrast agent, lowest amount of radiation exposure, or combination thereof) may be selected. In some embodiments, the operational setting providing the lowest dosage while satisfying a constraint may be selected.

At 216, a contrast agent (if desired or called for) is introduced to the patient being scanned. The contrast agent may be injected into the patient. In some embodiments, an automated injector may operate in conjunction with a scanning system to autonomously control administration of a contrast agent or agents. In some embodiments, instructions may be provided to a user manually changing or controlling an amount of contrast agent or agents administered to a patient.

At 218, a scan is performed on the object. The scan may be performed using the operational setting selected at 214. The operational setting may include one or more of a tube voltage, tube current, contrast agent (presence, type, and/or amount), or the like. Scanning information or data may be acquired during the scan from a detector upon which x-rays impinge after passing through the object.

Thus, embodiments disclosed herein provide for improved ease of use, automatic selection of one or more scanning operational parameters (e.g., tube voltage, amount of contrast agent, or the like), and improved dosage control (e.g., minimized or reduced diagnostic dosages corresponding to radiation and/or contrast agent). For example, as discussed herein, a practitioner may input a reference setting corresponding to an established protocol and/or a satisfactory image quality. Systems and methods of various embodiments discussed herein provide for automatic adjustment of one or more settings corresponding to a reference setting to reduce a diagnostic dosage while still providing an acceptable image quality (e.g., an image quality that is equivalent, with respect to a particular mode, to an image quality obtained using a reference setting).

Figure 3:
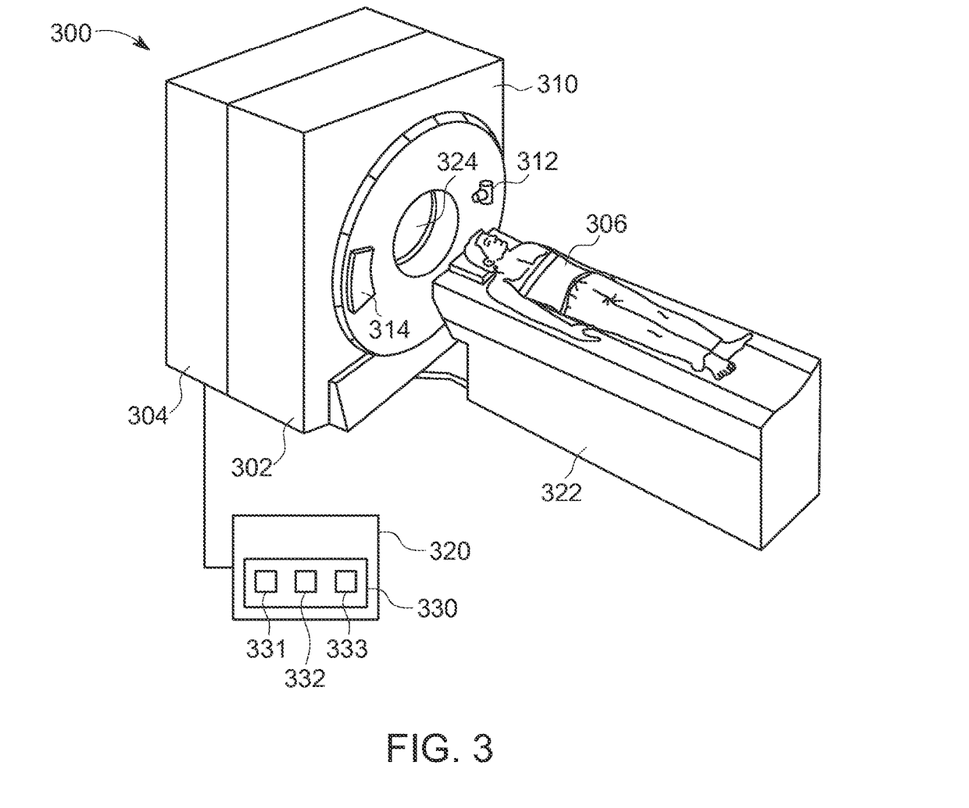
FIG. 3 is a pictorial view of an exemplary imaging system formed in accordance with various embodiments.

Various methods and algorithms described herein are used to select operational settings for a scan to be performed, and may be embodied as a set of instructions that are stored on a computer and implemented using, for example, a module 330, shown in FIG. 3, software, hardware, a combination thereof, and/or a tangible non-transitory computer readable medium. In one embodiment, a tangible non-transitory computer readable medium excludes signals.

Figure 4:
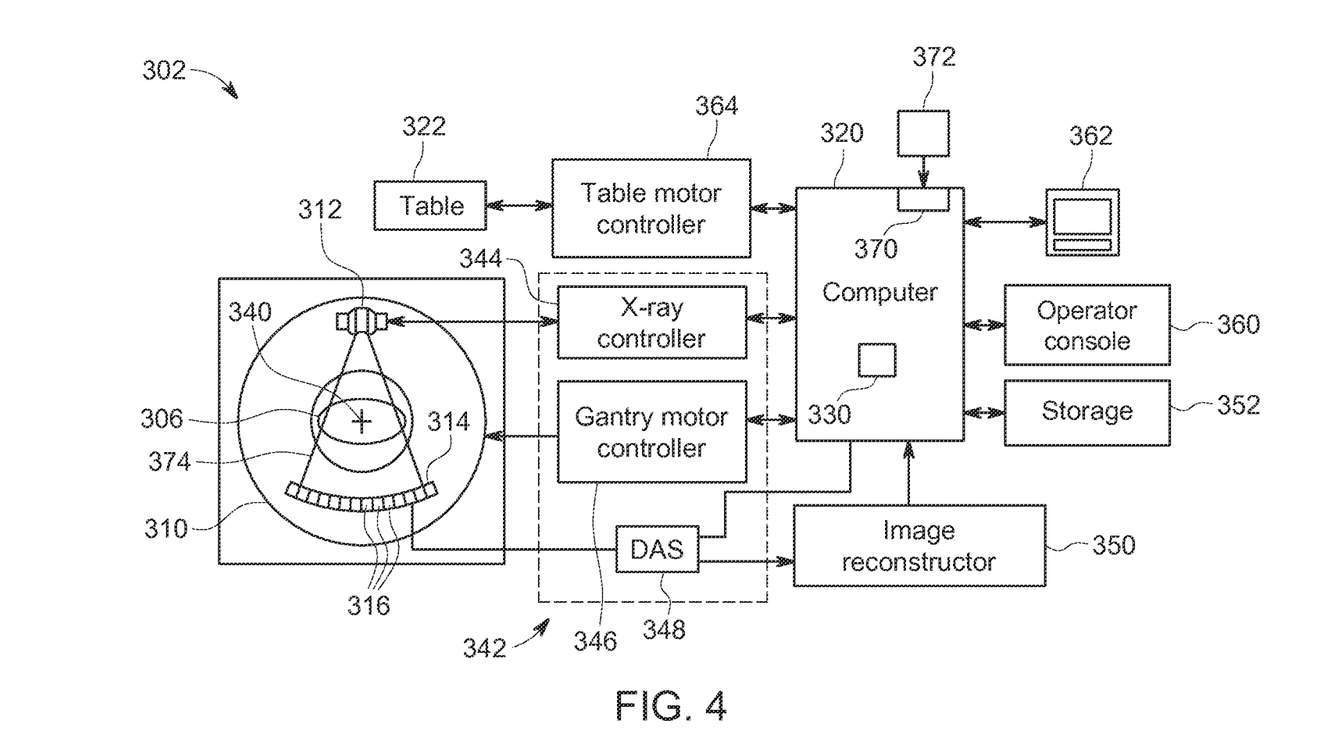
FIG. 4 is a block schematic diagram of the system illustrated in FIG. 3.

FIG. 3 is a pictorial view of an exemplary imaging system 300 that is formed in accordance with various embodiments. FIG. 4 is a block schematic diagram of a portion of the multi-modality imaging system 300 shown in FIG. 3. The imaging system may be embodied as a computed tomography (CT) imaging system, a dual energy x-ray absorptiometry (DEXA) system, a positron emission tomography (PET) imaging system, a magnetic resonance imaging (MRI) system, an ultrasound imaging system, an x-ray imaging system, a single photon emission computed tomography (SPECT) imaging system, an interventional C-Arm tomography imaging system, a CT system for a dedicated purpose such as extremity or breast scanning, and combinations thereof, among others. In the exemplary embodiment, the system 300 is described with respect to a CT imaging system.

Although various embodiments are described in the context of an exemplary dual modality imaging system that includes a computed tomography (CT) imaging system and a positron emission tomography (PET) imaging system, it should be understood that other imaging systems capable of performing the functions described herein are contemplated as being used. Moreover, the various methods described herein may be implemented with a stand-alone CT imaging system.

A multi-modality imaging system 300 is illustrated, and includes a CT imaging system 302 and a PET imaging system 304. The imaging system 300 allows for multiple scans in different modalities to facilitate an increased diagnostic capability over single modality systems. In one embodiment, the exemplary multi-modality imaging system 300 is a CT/PET imaging system 300. Optionally, modalities other than CT and PET are employed with the imaging system 300. For example, the imaging system 300 may be a standalone CT imaging system, a standalone PET imaging system, a magnetic resonance imaging (MRI) system, an ultrasound imaging system, an x-ray imaging system, and/or a single photon emission computed tomography (SPECT) imaging system, interventional C-Arm tomography, CT systems for a dedicated purpose such as extremity or breast scanning, and combinations thereof, among others.

The CT imaging system 302 includes a gantry 310 that has an x-ray source 312 that projects a beam of x-rays toward a detector array 314 on the opposite side of the gantry 310. The detector array 314 includes a plurality of detector elements 316 that are arranged in rows and channels that together sense the projected x-rays that pass through an object, such as the subject 306. The imaging system 300 also includes a computer 320 that receives the projection data from the detector array 314 and processes the projection data to reconstruct an image of the subject 306. In operation, operator supplied commands and parameters are used by the computer 320 to provide control signals and information to reposition a motorized table 322. More specifically, the motorized table 322 is utilized to move the subject 306 into and out of the gantry 310. Particularly, the table 322 moves at least a portion of the subject 306 through a gantry opening 324 that extends through the gantry 310.

The imaging system 300 also includes a module 330 that is configured to implement various methods and algorithms described herein. The module 330 may be implemented as a piece of hardware that is installed in the computer 320. Optionally, the module 330 may be implemented as a set of instructions that are installed on the computer 320. The set of instructions may be stand-alone programs, may be incorporated as subroutines in an operating system installed on the computer 320, may be functions in an installed software package on the computer 320, and the like. It should be understood that the various embodiments are not limited to the arrangements and instrumentality shown in the drawings. In the illustrated embodiment, the module 330 includes an identification module 331, an analysis module 332, and a determination module 333. It may be noted that the modules 331, 332, 333 may be stand-alone units, may be incorporated as sub-modules into a single module (e.g., module 330), or one or more aspects of one or more of the modules 331, 332, 333 may be combined with or integrated with other modules as a consolidated unit or unit, or may split among separate hardware units.

The identification module 331 of the illustrated embodiment is configured to identify a scanning mode of operation. The mode of operation may be a reference scanning mode corresponding to a protocol and/or one or more parameters entered by a practitioner or corresponding to an entry by a practitioner. The mode of operation may specify, for example, one or more of a tube voltage, tube current, noise index, or the like. In some embodiments, the identification module may be configured to identify a reference scanning technique. The reference scanning technique may correspond to, for example, a tissue or tissues to be scanned, a portion of a patient body to be scanned, an indication of whether or not contrast agent is used, a type of contrast agent used, an amount of contrast agent used, a type of information to be acquired by the scan or a purpose for which the scan is to be employed, or the like. The scanning mode of operation and/or scanning reference technique may be identified directly or directly using information input by a practitioner. For example, a practitioner may input one or more of a tube voltage, tube current, noise index, portion of body to be scanned, purpose of scan, or the like. As another example, a practitioner may specify (e.g., select from a list) a particular protocol (e.g., angiogram, liver scan, head injury, lesion analysis, sinus study, brain scan, chest scan, chest scan for identification of potential tumors, chest scan for identification of fluid accumulation, or the like), and the identification module may determine the scanning mode of operation based on the specified protocol. In various embodiments, protocols may be specified at varying levels of specificity. For example, a protocol may indicated a portion of the body to be scanned, or may indicate a portion of the body to be scanned as well as the purpose of the scan.

In the illustrated embodiment, the analysis module 332 is configured to determine an attenuation for an object for a scan to be performed. For example, using data collected during a scout scan, the analysis module 332 may determine the attenuation for a particular patient about to be scanned. Alternatively or additionally, an attenuation may be determined using alternate techniques. For example, an attenuation may be calculated, estimated, or otherwise determined using one or more of a patient height, patient weight, patient body mass index (BMI), patient diameter, or the like.

The determination module 333 may be configured to determine an image contrast (e.g., a contrast level resulting in an image for a given operational parameter or parameters of a scan) for each of plural setting combinations. A setting combination may include one or more of a tube voltage, tube current, attenuation, mode of operation, or the like. For example, a plurality of tube voltage settings or stations may be used. In some embodiments, a contrast level for a first setting corresponding to a given mode of operation and a tube voltage of about 80 kV, a contrast level for a second setting corresponding to the given mode of operation and a tube voltage of about 100 kV, a contrast level for a third setting corresponding to the given mode of operation and a tube voltage of about 120 kV, a contrast level for a fourth setting corresponding to the given mode of operation and a tube voltage of about 140 kV may be determined. In various embodiments, additional or alternative voltage levels, for example, may be employed.

The determination module 333 may also be configured to determine a corresponding tolerable (e.g., acceptable) noise (e.g., noise index or other measure of noise level) for the image contrast for each of the setting combinations based on the scanning mode of operation. For example, for a given scanning mode of operation, a relationship describing an acceptable change (e.g., increase) in noise for a corresponding change (e.g., increase) in contrast may be defined. Factors that may affect the relationship include, for example, type of equipment used, type of software used to reconstruct an image using data from a scan, type of tissue or tissues to be scanned, size of patient, attenuation of patient, purpose of the scan, user preferences, or the like. The relationship may be one or more of a scaling relationship, a weighted relationship, or the like.

Further, the determination module 333 in the illustrated embodiment is configured to determine a corresponding diagnostic dosage for each setting combination. The diagnostic dosages (e.g., there may be a particular diagnostic dosage determined for each particular setting combination) correspond to the image contrast and tolerable noise for the corresponding setting combination. In one example scenario, a given setting combination may include a tube voltage setting. The tube voltage setting defines, influences, or otherwise corresponds to the image contrast resulting from a scan performed at the given tube voltage setting. A noise index for a tolerable noise may then be determined using a relationship between image contrast (e.g., change in image contrast) and noise (e.g., change in noise). Using the noise level thus determined, a tube current corresponding to the noise level may then be determined. Next, the determination module 333 may use the tube voltage for the given setting combination along with the resulting determined tube current to determine a dosage of radiation for the given setting combination.

The determination of radiation dosage may then be performed for each of a plurality of setting combinations. In various embodiments, the determination module 333 may be configured to select a scanning operational setting for the scan to be performed at using the dosages determined for each of the setting combinations. For example, the operational setting providing the lowest radiation dosage while still providing acceptable image quality (as defined by a relationship between contrast and noise as described herein) may be selected. In some embodiments, the operational setting resulting in the lowest dosage that satisfies one or more constraints may be selected. For example, a minimum contrast and/or maximum noise level may be used to constrain the selection. As another example, a setting that differences from a reference setting (e.g., a reference setting entered by a practitioner) may be used only if that particular setting results in a change of radiation dosage exceeding a threshold dosage improvement. For example, reference settings input by a practitioner (or reference settings determined using or otherwise corresponding to settings input by a practitioner) may be adjusted to a determined operational setting only if the adjustment results in a reduction of dosage by at least about ten percent. Other thresholds may be employed in various embodiments. Further, the effect of a variance of one or more other settings (additionally or alternatively to tube voltage) on a dosage may be evaluated using similar principles as discussed herein. For example, in some embodiments, settings including variations in contrast agent may be evaluated to select a setting providing a reduced or minimized dosage of contrast agent. Thus, in some embodiments, a diagnostic dosage to be determined may include a contrast agent dosage. In some embodiments, a diagnostic dosage to be determined may include a combination of a radiation dosage and contrast agent dosage, which may be combined, for example, in a weighted combination.

As discussed above, the detector 314 includes a plurality of detector elements 316. Each detector element 316 produces an electrical signal, or output, that represents the intensity of an impinging x-ray beam and hence allows estimation of the attenuation of the beam as it passes through the subject 306. During a scan to acquire the x-ray projection data, the gantry 310 and the components mounted thereon rotate about a center of rotation 340. FIG. 4 shows only a single row of detector elements 316 (i.e., a detector row). However, the multislice detector array 314 includes a plurality of parallel detector rows of detector elements 316 such that projection data corresponding to a plurality of slices can be acquired simultaneously during a scan.

Rotation of the gantry 310 and the operation of the x-ray source 312 are governed by a control mechanism 342. The control mechanism 342 includes an x-ray controller 344 that provides power and timing signals to the x-ray source 312 and a gantry motor controller 346 that controls the rotational speed and position of the gantry 310. A data acquisition system (DAS) 348 in the control mechanism 342 samples analog data from detector elements 316 and converts the data to digital signals for subsequent processing. For example, the subsequent processing may include utilizing the module 330 to implement the various methods described herein. An image reconstructor 350 receives the sampled and digitized x-ray data from the DAS 348 and performs high-speed image reconstruction. The reconstructed images are input to the computer 320 that stores the image in a storage device 352. Optionally, the computer 320 may receive the sampled and digitized x-ray data from the DAS 348 and perform various methods described herein using the module 330. The computer 320 also receives commands and scanning parameters from an operator via a console 360 that has a keyboard. An associated visual display unit 362 allows the operator to observe the reconstructed image and other data from the computer 320. The operator supplied commands and parameters are used by the computer 320 to provide control signals and information to the DAS 348, the x-ray controller 344 and the gantry motor controller 346. In addition, the computer 320 operates a table motor controller 364 that controls the motorized table 322 to position the subject 306 in the gantry 310. Particularly, the table 322 moves at least a portion of the subject 306 through the gantry opening 324 as shown in FIG. 3.

Referring again to FIG. 4, in one embodiment, the computer 320 includes a device 370, for example, a floppy disk drive, CD-ROM drive, DVD drive, magnetic optical disk (MOD) device, or any other digital device including a network connecting device such as an Ethernet device for reading instructions and/or data from a computer-readable medium 372, such as a CD-ROM, a DVD or another digital source such as a network or the Internet, as well as yet to be developed digital means. In another embodiment, the computer 320 executes instructions stored in firmware (not shown). The computer 320 is programmed to perform functions described herein, and as used herein, the term computer is not limited to just those integrated circuits referred to in the art as computers, but broadly refers to computers, processors, microcontrollers, microcomputers, programmable logic controllers, application specific integrated circuits, and other programmable circuits, and these terms are used interchangeably herein.

In the exemplary embodiment, the x-ray source 312 and the detector array 314 are rotated with the gantry 310 within the imaging plane and around the subject 306 to be imaged such that the angle at which an x-ray beam 374 intersects the subject 306 constantly changes. A group of x-ray attenuation measurements, i.e., projection data, from the detector array 314 at one gantry angle is referred to as a "view". A "scan" of the subject 306 comprises a set of views made at different gantry angles, or view angles, during one revolution of the x-ray source 312 and the detector 314. In a CT scan, the projection data is processed to reconstruct an image that corresponds to a two dimensional slice taken through the subject 306.

Exemplary embodiments of a multi-modality imaging system are described above in detail. The multi-modality imaging system components illustrated are not limited to the specific embodiments described herein, but rather, components of each multi-modality imaging system may be utilized independently and separately from other components described herein. For example, the multi-modality imaging system components described above may also be used in combination with other imaging systems.

Thus, embodiments discussed herein provide for a reduction or minimization of a potentially harmful, inconvenient, expensive, or otherwise undesirable diagnostic dosage, improved ease of use of tube voltage selection, automatic selection or adjustment of tube voltage and/or current to reduce or minimize diagnostic dosage, and/or the automatic selection of imaging parameters to produce a reconstructed image having an image quality tailored for particular practitioners.

It should be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid state drive, optical drive, and/or the like. The storage device may also be other similar means for loading computer programs or other instructions into the computer or processor.

As used herein, the term "computer" may include any processor-based or microprocessor-based system including systems using microcontrollers, reduced instruction set computers (RISC), application specific integrated circuits (ASICs), logic circuits, GPUs, FPGAs, and any other circuit or processor capable of executing the functions described herein. The above examples are exemplary only, and are thus not intended to limit in any way the definition and/or meaning of the term "computer". The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the invention. The set of instructions may be in the form of a software program. The software may be in various forms such as system software or application software, which may be a non-transitory computer readable medium. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated, but a viewable image is not. Therefore, as used herein the term "image" broadly refers to both viewable images and data representing a viewable image. However, many embodiments generate, or are configured to generate, at least one viewable image.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions and types of materials described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A computed tomography (CT) imaging system configured to utilize X-rays, the CT imaging system comprising at least one processor and a tangible and non-transitory computer readable medium, the at least one processor directed by instructions stored on the tangible and non-transitory computer readable medium to:
identify a scanning mode of operation for a scan to be performed on an object, the scanning mode of operation corresponding to at least one of a clinical task or clinical application, the scanning mode of operation specifying one or more parameters that influences a relationship between contrast and tolerable noise;
determine an attenuation for the object for the scan to be performed on the object;
determine an image contrast for each of plural setting combinations for the scan to be performed on the object, wherein each of the setting combinations is for a same type of scan on a same type of tissue;
determine a corresponding tolerable noise level for the image contrast for each of the setting combinations based on the scanning mode of operation, wherein a contrast to noise ratio (CNR) corresponding to the tolerable noise levels varies among the setting combinations, wherein each tolerable noise level is for the same type of scan on the same type of tissue for the setting combinations;
determine a corresponding current for each tolerable noise level based on the tolerable noise level;
determine a corresponding diagnostic dosage for each setting combination for the scan to be performed on the object based on the corresponding current and a corresponding voltage, the diagnostic dosages corresponding to the image contrast and tolerable noise for the corresponding setting combination;
select an operational setting for the scan to be performed from among the setting combinations using the dosages determined; and
perform the scan using the operational setting for the scan to be performed.

2. The imaging system of claim 1, wherein the at least one processor is further instructed to identify a reference scanning technique, wherein the determination module is configured to determine the tolerable noise for each of the setting combinations using a scaling relationship between noise and image contrast, wherein the tolerable noise for a given setting combination is determined by adjusting a tolerable noise corresponding to the reference scanning technique adjusted by an amount corresponding to at least one scaling factor.

3. The imaging system of claim 2, wherein the scaling relationship corresponds to a scaling factor described by sf $=\Delta NI/\Delta IC$, where sf is the scaling factor, $\Delta IC$ corresponds to a change in image contrast, and $\Delta NI$ corresponds to an acceptable increase in noise corresponding to an increase in image contrast.

4. The imaging system of claim 2, wherein the scaling relationship uses a scaling factor that corresponds to a weighted combination of a plurality of materials.

5. The imaging system of claim 1, wherein the setting combination includes a tube voltage setting, wherein the image contrast is determined using the tube voltage setting, wherein the tolerable noise is determined using the image contrast, and wherein the diagnostic dosage comprises a radiation dosage corresponding to the tube voltage setting and a tube current setting, the tube current setting corresponding to the tolerable noise.

6. The imaging system of claim 1, wherein the at least one processor is further instructed to select a setting combination of the plural setting combinations that results in a minimum diagnostic dosage within one or more of a system constraint or a dosage constraint.

7. The imaging system of claim 1, wherein the attenuation is determined using scout scan information acquired during a scout scan performed on the object before the scan to be performed.

8. The imaging system of claim 1, wherein the diagnostic dosage comprises a radiation dosage corresponding to the tube voltage setting and a tube current setting, the tube current setting corresponding to the tolerable noise.

9. The imaging system of claim 1, wherein the diagnostic dosage comprises a contrast agent dosage.

10. The imaging system of claim 1, wherein the diagnostic dosage corresponds to a combination of a contrast agent dosage and a radiation dosage.

11. A method for selecting settings for a computed tomography (CT) scan to be performed on an object, the CT scan to be performed using X-rays, the method comprising:
identifying a scanning mode of operation for the CT scan to be performed, the scanning mode of operation corresponding to at least one of a clinical task or clinical application, the scanning mode of operation specifying one or more parameters that influences a relationship between contrast and tolerable noise;
determining an attenuation for the object for the CT scan to be performed;
determining an image contrast for each of plural setting combinations for the CT scan to be performed, wherein each of the setting combinations is for a same type of scan on a same type of tissue;
determining a corresponding tolerable noise level for the image contrast for each of the setting combinations, wherein a contrast to noise ratio (CNR) corresponding to the tolerable noise levels varies among the setting combinations, wherein each tolerable noise level is for the same type of scan on the same type of tissue for the setting combinations;
determining a corresponding current for each tolerable noise level based on the tolerable noise level;
determining a corresponding diagnostic dosage for each setting combination for the CT scan to be performed based on the corresponding current and a corresponding voltage, the diagnostic dosages corresponding to the image contrast and tolerable noise for the corresponding setting combination;
selecting an operational setting for the CT scan to be performed from among the setting combinations using the dosages determined; and
performing the CT scan using the operational setting for the scan to be performed.

12. The method of claim 11, further comprising performing the CT scan using the setting combination selected using the dosages determined.

13. The method of claim 11, further comprising identifying a reference scanning technique, wherein the determining the tolerable noise for each of the setting combinations uses a scaling relationship between noise and image contrast, wherein the tolerable noise for a given setting combination is determined by adjusting a tolerable noise corresponding to the reference scanning technique adjusted by an amount corresponding to at least one scaling factor.

14. The method of claim 13, wherein the scaling relationship corresponds to a scaling factor described by sf = $\Delta NI/\Delta IC$, where sf is the scaling factor, $\Delta IC$ corresponds to a change in image contrast, and $\Delta NI$ corresponds to an acceptable increase in noise corresponding to an increase in image contrast.

15. The method of claim 13, wherein the scaling relationship uses a scaling factor that corresponds to a weighted combination of a plurality of materials.

16. The method of claim 11, wherein the setting combination includes a tube voltage setting, wherein the image contrast is determined using the tube voltage setting, wherein the tolerable noise is determined using the image contrast, and wherein the diagnostic dosage comprises a radiation dosage corresponding to the tube voltage setting and a tube current setting, the tube current setting corresponding to the tolerable noise.

17. The method of claim 11, wherein the diagnostic dosage comprises a contrast agent dosage.

18. The method of claim 11, wherein the diagnostic dosage corresponds to a combination of a contrast agent dosage and a radiation dosage.

19. A tangible and non-transitory computer readable medium comprising one or more computer software modules configured to direct a processor to:
identify a scanning mode of operation for a computed tomography (CT) scan to be performed on an object, the scanning mode of operation corresponding to at least one of clinical task or clinical application, the scanning mode of operation specifying one or more parameters that influences a relationship between contrast and tolerable noise;
determine an attenuation for an object for the CT scan to be performed, the CT scan to be performed using X-rays;
determine an image contrast for each of plural setting combinations for the CT scan to be performed, wherein each of the setting combinations is for a same type of scan on a same type of tissue;
determine a corresponding tolerable noise level for the image contrast for each of the setting combinations, wherein a contrast to noise ratio (CNR) corresponding to the tolerable noise levels varies among the setting combinations, wherein each tolerable noise level is for the same type of scan on the same type of tissue for the setting combinations;
determine a corresponding current for each tolerable noise level based on the tolerable noise level;
determine a corresponding diagnostic dosage for each setting combination for the CT scan to be performed based on the corresponding current and a corresponding voltage, the diagnostic dosages corresponding to the image contrast and tolerable noise for the corresponding setting combination;
select an operational setting for the CT scan to be performed from among the setting combinations using the dosages determined; and
perform the CT scan using the operational setting for the scan to be performed.

20. The tangible and non-transitory computer readable medium of claim 19, wherein the one or more software modules are further configured to direct the processor to identify a reference scanning technique, and to determine the tolerable noise for each of the setting combinations using a scaling relationship between noise and image contrast, wherein the tolerable noise for a given setting combination is determined by adjusting a tolerable noise corresponding to the reference scanning technique adjusted by an amount corresponding to at least one scaling factor.

21. The tangible and non-transitory computer readable medium of claim 20, wherein the scaling relationship corresponds to a scaling factor described by sf = $\Delta NI/\Delta IC$, where sf is the scaling factor, $\Delta IC$ corresponds to a change in image contrast, and $\Delta NI$ corresponds to an acceptable increase in noise corresponding to an increase in image contrast.

22. The tangible and non-transitory computer readable medium of claim 20, wherein the scaling relationship uses a scaling factor that corresponds to a weighted combination of a plurality of materials.

23. The tangible and non-transitory computer readable medium of claim 19, wherein the setting combination includes a tube voltage setting, wherein the image contrast is determined using the tube voltage setting, wherein the tolerable noise is determined using the image contrast, and wherein the diagnostic dosage comprises a radiation dosage corresponding to the tube voltage setting and a tube current setting, the tube current setting corresponding to the tolerable noise.

24. The tangible and non-transitory computer readable medium of claim 19, wherein the diagnostic dosage comprises a contrast agent dosage.

25. The tangible and non-transitory computer readable medium of claim 19, wherein the diagnostic dosage corresponds to a combination of a contrast agent dosage and a radiation dosage.

26. The imaging system of claim 1, wherein the CNR is selected from a range based on a user tolerance for diagnostic dosage.

27. The imaging system of claim 1, further comprising a display configured to display an image that has been reconstructed using information acquired during the CT scan using the operational settings.

28. The imaging system of claim 2, wherein the at least one scaling factor comprises a range of scaling factors.

* * * * *